(12) United States Patent
Schöchl et al.

(10) Patent No.: US 11,935,649 B2
(45) Date of Patent: Mar. 19, 2024

(54) METHOD FOR WEB-BASED DATA TRANSFER FOR A DENTAL OR DENTAL-SURGICAL TREATMENT OR DIAGNOSIS SYSTEM AND SUCH A TREATMENT OR DIAGNOSIS SYSTEM

(71) Applicant: W&H Dentalwerk Bürmoos GmbH, Bürmoos (AT)

(72) Inventors: Andreas Schöchl, Mattsee (AT); Michael Reiter, Elsbethen (AT)

(73) Assignee: W&H Dentalwerk Burmoos GmbH, Burmoos (AT)

( * ) Notice: Subject to any disclaimer, the term of this patent is extended or adjusted under 35 U.S.C. 154(b) by 0 days.

(21) Appl. No.: 16/675,869

(22) Filed: Nov. 6, 2019

(65) Prior Publication Data
US 2020/0143941 A1    May 7, 2020

(30) Foreign Application Priority Data
Nov. 7, 2018   (EP) .................................... 18204816

(51) Int. Cl.
  G16H 40/67   (2018.01)
  G16H 20/40   (2018.01)
  G16H 50/20   (2018.01)
(52) U.S. Cl.
  CPC ............. *G16H 40/67* (2018.01); *G16H 20/40* (2018.01); *G16H 50/20* (2018.01)
(58) Field of Classification Search
  CPC ....... G06Q 50/22–24; G06Q 50/20–26; G16H 40/67; G16H 20/40; G16H 50/20
  (Continued)

(56) References Cited

U.S. PATENT DOCUMENTS 9,345,061 B1 *   5/2016  Evans ..................... G06F 3/165
2003/0078806 A1   4/2003  Kudryk et al.
(Continued)

FOREIGN PATENT DOCUMENTS

CA   2519941 A1 * 10/2004   ........... A61C 1/0015
CA   2519941 C  *  5/2011   ........... A61C 1/0015
(Continued)

OTHER PUBLICATIONS

C. Parga, X. Li and W. Yu, "Smartphone-Based Human Machine Interface with Application to Remote Control of Robot Arm," 2013 IEEE International Conference on Systems, Man, and Cybernetics, 2013, pp. 2316-2321, doi: 10.1109/SMC.2013.396. (Year: 2013).*
(Continued)

*Primary Examiner* — Jason S Tiedeman
*Assistant Examiner* — Jessica Marie Webb
(74) *Attorney, Agent, or Firm* — Wood, Phillips, Katz, Clark & Mortimer

(57) ABSTRACT

Methods and systems for transferring at least one data set between a dental or dental-surgical treatment or diagnosis device and an external memory element located outside the dental or dental-surgical treatment or diagnosis device, wherein the at least one data set is transferred in a web-based manner via the Internet and a cloud computing network comprising the external memory element. A corresponding dental or dental-surgical treatment or diagnosis system comprises a dental or dental-surgical treatment or diagnosis device and a transmitting and receiving device for communicatively connecting to a remote-control human-machine interface. The transmitting and receiving device is designed for providing a web-based connection via the Internet and a cloud computing network to the remote-control human-machine interface.

26 Claims, 1 Drawing Sheet

(58) Field of Classification Search
USPC .......................................................... 705/3
See application file for complete search history.

(56) References Cited

U.S. PATENT DOCUMENTS

| | | | |
|---|---|---|---|
| 2010/0105009 A1 | 4/2010 | Karkar et al. | |
| 2010/0151417 A1* | 6/2010 | Nilsson | A61C 7/002 |
| | | | 700/118 |
| 2010/0227296 A1 | 9/2010 | Mandelis et al. | |
| 2013/0110527 A1 | 5/2013 | Chen | |
| 2013/0116805 A1* | 5/2013 | Frochaux | A61B 6/14 |
| | | | 700/83 |
| 2013/0171580 A1 | 7/2013 | Van Lierde et al. | |
| 2014/0115487 A1* | 4/2014 | Sandler | H04M 1/72412 |
| | | | 715/740 |
| 2014/0379913 A1* | 12/2014 | Niimura | H04L 67/34 |
| | | | 709/225 |
| 2015/0057675 A1* | 2/2015 | Akeel | G16H 50/50 |
| | | | 901/47 |
| 2016/0012182 A1* | 1/2016 | Golay | G16H 40/20 |
| | | | 705/3 |
| 2016/0038092 A1* | 2/2016 | Golay | G16H 30/40 |
| | | | 433/24 |
| 2016/0086514 A1 | 3/2016 | Washburn et al. | |
| 2016/0220316 A1 | 8/2016 | Daon et al. | |
| 2017/0046486 A1* | 2/2017 | Cunningham | G06F 3/0482 |
| 2017/0091411 A1* | 3/2017 | Schoenecker | G16H 20/30 |
| 2017/0364659 A1* | 12/2017 | Choi | A61C 13/0004 |
| 2018/0184891 A1* | 7/2018 | Elazar | G06T 7/11 |
| 2018/1848914 | 7/2018 | Elazar et al. | |
| 2018/0256021 A1* | 9/2018 | Gill | A61B 18/24 |
| 2019/0029757 A1* | 1/2019 | Roh | A61B 90/37 |
| 2020/0082934 A1* | 3/2020 | Venkataraman | G16H 40/63 |
| 2020/0105385 A1* | 4/2020 | Gass | G16H 10/60 |

FOREIGN PATENT DOCUMENTS

| | | | | |
|---|---|---|---|---|
| CA | 2868737 A1 | * | 10/2012 | ........... A61B 18/082 |
| EP | 2431004 A1 | * | 3/2012 | ........... A61C 1/0015 |
| EP | 3649978 A1 | * | 5/2020 | ............ G16H 50/20 |
| JP | 2001/258044 A | | 9/2001 | |
| JP | 2001-306691 A | | 11/2001 | |
| JP | WO2018193936 A | | 2/2020 | |
| KR | 20160122674 A | | 10/2016 | |
| KR | 20170082676 A | | 7/2017 | |
| WO | WO-0119248 A1 | * | 3/2001 | ............ A61C 19/04 |
| WO | 2015154125 A1 | | 10/2015 | |
| WO | WO2016/059550 | | 4/2016 | |
| WO | 2016093984 A1 | | 6/2016 | |
| WO | WO-2017063071 A1 | * | 4/2017 | ........... A61B 5/0053 |
| WO | WO-2018132912 A1 | * | 7/2018 | ............ A61C 19/06 |
| WO | WO-2018193936 A1 | * | 10/2018 | ............ A61C 19/04 |

OTHER PUBLICATIONS (N.a.), "Remote HMI and Remote Access Features", 2017, Wayback Machine, all pages, https://web.archive.org/web/20171002071640/ https://www.automationdirect.com/c-more/features/remote-hmi-and-remote-access#remotehmi (Year: 2017).*
European Search Report for European Application No. 1820,4816, dated Aug. 12, 2019.

* cited by examiner

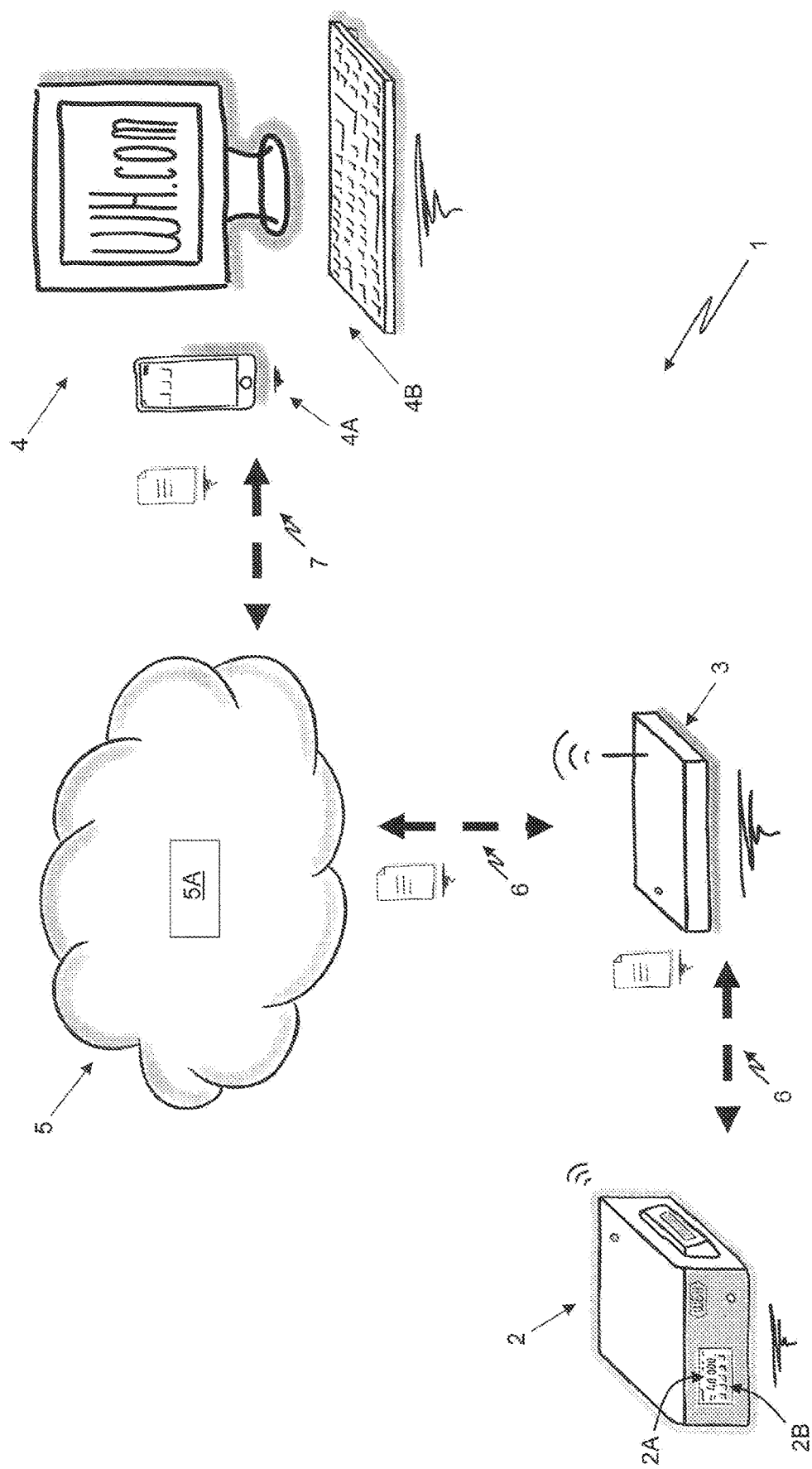

METHOD FOR WEB-BASED DATA TRANSFER FOR A DENTAL OR DENTAL-SURGICAL TREATMENT OR DIAGNOSIS SYSTEM AND SUCH A TREATMENT OR DIAGNOSIS SYSTEM

CROSS REFERENCE TO RELATED APPLICATION

The present application claims priority from pending European Patent Application No. 18204816.5, filed Nov. 7, 2018, which is incorporated herein by reference.

FIELD

The present invention concerns a method for web-based transfer of at least one data set for a dental or dental-surgical treatment or diagnosis system and such a treatment or diagnosis system.

DESCRIPTION OF PRIOR ART

A dental treatment device known from patent application US 2013/0116805 A1, which is incorporated herein by reference, can be controlled via a portable human-machine interface, for example a smartphone. For this purpose, the programs and data required for control are stored locally on the smartphone. Data exchange between the dental treatment device and the smartphone takes place via a local communication link.

A disadvantage of this treatment system is that the control of the dental treatment device is restricted to the human-machine interface where the required programs and data are stored. If this human-machine interface is not available, the dental treatment device cannot be controlled or data cannot be retrieved from said device.

SUMMARY

Based on the foregoing it would be advantageous to create a method of transferring at least one data set for a dental or dental-surgical treatment or diagnostic system, and a corresponding dental or dental-surgical treatment or diagnosis system allowing less restricted access to the dental or dental-surgical treatment or diagnosis system. In particular, communication with the dental or dental-surgical treatment or diagnosis system should not be tied to a specific human-machine interface.

The method, in particular computer-implemented, for transferring at least one data set between a dental or dental-surgical treatment or diagnosis device and an external memory element disposed outside the dental or dental-surgical treatment or diagnosis device comprises the step that the at least one data set is transferred in a web-based manner via the Internet and a cloud computing network having the external memory element.

Due to the web-based transfer of the at least one data set and the use of a cloud computing network, it is advantageously possible to access the at least one data set independently of time and place and without being restricted to a specific remote-control human-machine interface. It is also preferable that a plurality of persons have access to the at least one data set.

The external memory element is designed as part of the cloud computing network and is therefore located remotely from the dental or dental-surgical treatment or diagnosis device and/or remote-control human-machine interface.

The external memory element is in particular configured to store the at least one data set transferred in a web-based manner and/or for providing at least one stored data set for web-based transfer to the dental or dental-surgical treatment or diagnosis device. Particularly preferred, the method of transferring at least one data set can include a bidirectional method wherein data sets are transferred via the Internet in both directions between the dental or dental-surgical treatment or diagnosis device and the external memory element. Said measures advantageously permit a complete data flow in both directions.

The at least one data set transferred through the Internet and a cloud computing network and/or stored or to be stored by the external memory element comprises, for example, operating or treatment data or at least one value of at least one operating parameter generated during operation or in connection with an operation of the dental or dental-surgical treatment or diagnosis device or during treatment or in connection with a treatment by the dental or dental-surgical treatment or diagnosis device. The at least one data set alternatively or additionally comprises, for example, operational or treatment data or at least one value of at least one operational parameter required for operating the dental or dental-surgical treatment or diagnosis device or required for treatment with the dental or dental-surgical treatment or diagnosis device and/or provided prior to operating or treating.

The external memory element is preferably additionally configured to store at least one data set or at least one value of at least one operating parameter and for providing said value or data set in particular for web-based transfer to the dental or dental-surgical treatment or diagnosis device, wherein said data set or value can be or is entered via a remote-control human-machine interface described in detail below. The remote-control human-machine interface is preferably connected or can be connected to the cloud computing network via the Internet. This makes it advantageously possible for a user to enter or change data sets or values individually.

The at least one data set referred to above, transferred via the Internet and a cloud computing network, and/or stored or storable by the memory element, and/or provided for web-based transfer, comprises technical data or technical values of a parameter, for example, preferably a torque value, a torque limit value, a speed value, a speed limit value, a transmission ratio of a mechanical gear of the dental or dental-surgical treatment or diagnosis device, a volume flow of an operating or cooling medium, a performance of a component of the dental or dental-surgical treatment or diagnosis device, for example of a motor or a pump, a current or voltage value of a component of the dental or dental-surgical treatment or diagnosis device, and similar data.

The at least one data set alternatively or additionally comprises, for example, non-technical data or values, preferably information about the user of the dental or dental-surgical treatment or diagnosis device, in particular an identification code; information about the treated patient, in particular an identification code; information about a selected or used operating program of the dental or dental-surgical treatment or diagnosis device; information about the dental or dental-surgical treatment or diagnosis device, in particular a serial number; information about an implant (implanted or to be implanted), in particular the manufacturer, a serial number, and/or the expiration date thereof; an error message; or similar data or values.

Preferably the at least one data set comprises at least parts of a so-called library, for example an implant library or a tool library, preferably a library of endodontic files. Such a library comprises in particular a variety of data, values, and/or specifications for different elements. For example, an implant library comprises data or values for a plurality of implants, in particular from different manufacturers. Each implant in the library is preferably assigned one or more specific data or values, for example an implant designation (manufacturer name, identification code, etc.), the tooth position (according to the tooth scheme) for which the implant is intended, a torque value at which the implant is to be set, a maximum torque value at which the implant may be set, a transmission ratio of a gear of a dental contra-angle handpiece with which the implant is to be set, and/or similar data and values. The provision of such a library in the external memory element greatly simplifies the planning and/or execution of a dental or dental-surgical treatment for a user, as the user has easy access to the required element (implant, tool) and the associated data and value. Storing a library in the external memory element of the cloud computing network also has the advantage that the current library is always available to the user without the user having to maintain it, i.e., supplement or update it. Preferably the library or a part of it will be maintained, supplemented, and/or updated by a third party, for example a manufacturer of implants or tools or of the treatment or diagnosis device.

Preferably the at least one data set transferred via the Internet and a cloud computing network and/or storable by the external memory element comprises one or more dental or dental-surgical treatment plans, for example for implantation of a dental implant or for an endodontic treatment, wherein such a treatment plan preferably comprises a plurality of the data, data sets, and/or parameter values mentioned above. This advantageously makes it possible for the user to create a treatment plan independently of time and place and without restriction to a specific remote-control human-machine interface.

Preferably the at least one data set transferred via the Internet and a cloud computing network and/or storable by the external memory element comprises data for treatment or patient documentation or patient management, in particular personal data such as name, gender, age, address, contact data, medical information on preexisting conditions, treatments performed, diagnostic data, or similar data. This advantageously makes it possible for the user to access treatment or patient documentation or patient management, independent of time and place and without restriction to a specific remote-control human-machine interface.

The dental or dental-surgical treatment or diagnosis device preferably comprises at least one of the following elements: a straight or curved in particular cordless handpiece, contra-angle handpiece or handle element; a dental or dental-surgical supply and/or control device, in particular a table-top device, for operating a dental or dental-surgical handpiece, contra-angle handpiece, and/or instrument; a device for determining the stability of a set (dental) implant; a dental or dental-surgical treatment unit with a supply and/or control device and a patient chair.

The dental or dental-surgical treatment or diagnosis device comprises at least one of the following elements:
- an (internal) memory element for storing at least one data set, in particular one or more of the data sets mentioned above, particularly preferably the operating or treatment data and/or at least one treatment plan; the (internal) memory element is configured in particular for the storage of the at least one data set transferred in a web-based manner via the Internet and the cloud computing network from the external memory element, and/or for intermediate storage of at least one data set and/or parameter value, preferably an operating or treatment value (in particular mentioned above) of the treatment or diagnosis device (to be) transferred in a web-based manner via the Internet and the cloud computing network to the external memory element and thereby advantageously act as a data buffer in the case that the web-based data transfer to the cloud computing network is interrupted;
- a controller for the control or regulation of the treatment or diagnosis device and/or an instrument connected thereto; in particular for controlling or regulating on the basis of the at least one data set mentioned above and possibly stored in the internal memory, preferably on the basis of at least some of said operating or treatment data mentioned above, on the basis of at least a part of a library, and/or a treatment plan transferred in a web-based manner from the external memory element via the Internet and the cloud computing network;
- a display device for displaying at least one data set or parameter value, in particular the aforementioned at least one data set transferred in a web-based manner via the Internet and the cloud computing network, for example the operating or treatment data and/or at least a part of a treatment plan, as well as warnings, error messages, or similar data;
- a setting device, for example a button, slide, and/or touch screen, in particular for setting at least one value of an operating parameter of the dental or dental-surgical treatment or diagnosis device and/or for selecting an operating program or treatment plan; the setting device is preferably configured for setting or changing at least one value of the above-mentioned at least one data set transferred in a web-based manner by the Internet and the cloud-computing network, preferably of operating or treatment data, of at least one parameter, and/or of at least one treatment plan, wherein a change to said parameters and/or of at least one treatment plan is advantageously possible even after the web-based transfer;
- at least one sensor for detecting a measured value, for example a current sensor, temperature sensor, pressure sensor, conductivity sensor, or a humidity sensor; the measured value forms, for example, at least a part of the above-mentioned data set, that in particular is transferred in a web-based manner via the Internet and the cloud computing network, said data set preferably being stored in the external memory element of the cloud computing network;
- at least one media line for conducting an operating medium or a drive medium, in particular water or air,
- at least one electrical line for supplying an electrical consumer with electrical energy, for example an electric motor, a radiation source, and/or a sensor, and/or for transmitting measured values from a sensor of the dental or dental-surgical treatment or diagnosis device;
- a tool-holding device for preferably detachably retaining a treatment tool;
- a radiation source, for example an optical semiconductor element, for emitting electromagnetic radiation, in particular visible light and/or diagnostic radiation.

In addition to the external memory element, the cloud computing network preferably comprises at least further hardware and/or software elements, for example one of the following elements: a processor, a microcontroller in particular having one or more electronic circuits; one or more software programs or web applications in particular executable by at least one electronic circuit of the microcontroller, for storing, receiving, processing, sending, encrypting, decrypting, and/or providing the at least one data set or parameter value transferred via the Internet. The web application can in particular be called up and/or operated via the remote-control human-machine interface. The microcontroller and the external memory element are in particular electrically connected to each other so that the microcontroller can access the data sets and/or software stored in the external memory element.

Preferably, the at least one data set (transferred and/or stored in the external memory) is or can be displayed and/or accessed and/or processed via a remote-control human-machine interface communicatively connected or capable of connecting to the cloud computing network. Alternatively or additionally, it is also possible that a (further) data set is entered via the remote control human-machine interface and preferably stored in the external memory. Preferably, the remote-control human-machine interface is also communicatively connected (via the cloud computing network and the Internet) to the treatment or diagnosis device. The communicative connection of the remote-control human-machine interface to the cloud computing network can be established or accomplished in a wired and/or wireless manner.

Preferably, the remote-control human-machine interface comprises, for example, a mobile electronic device, in particular a mobile telephone, a portable computer, a laptop, a tablet computer, or similar devices, or a stationary electronic device, for example a personal computer.

Preferably, a web application stored in the cloud computing network is accessed via the remote-control human-machine interface for retrieving and/or displaying and/or editing the at least one data set stored in the external memory element and/or for entering and storing at least one data set in the external memory. Preferably, the remote-control human-machine interface comprises a web browser for accessing the web application.

Preferably, the at least one data set (transferred and/or stored) is processed by a microcontroller of the cloud computing network. Preferably, the cloud computing network comprises software and/or hardware for editing or processing the at least one data set, for example software for (graphically) displaying the at least one data set, for linking the at least one data set with already stored data, and/or for comparing different data sets. This advantageously increases the functionality of the treatment or diagnosis device.

Preferably, the external memory element comprises or stores software for planning a treatment or diagnosis with the dental or dental-surgical treatment or diagnosis device, wherein the at least one data set transferred in a web-based manner via the Internet and a cloud computing network comprises a treatment plan created by means of the software. The treatment plan preferably comprises one or more treatment or diagnostic steps. The treatment plan preferably comprises at least one of the operational or treatment data referred to above or at least one value of at least one operational parameter. Preferably the operating or treatment data or at least one value is entered by the user or selected from preset values. Preferably, a user creates one or more treatment plans and sends at least one of said treatment plans to one or more treatment or diagnosis devices.

Preferably, a user creates a plurality of treatment plans for a plurality of treatments or diagnoses, such as dental-surgical implantations, that he/she wishes to perform on the same dental or dental-surgical treatment or diagnosis device. Preferably, the user sends the plurality of treatment plans, in particular in the form of a (single) data package or data set, to the one treatment or diagnosis device, said device storing the plurality of treatment plans in an internal memory. Preferably, the user performs a plurality of treatments or diagnoses one after the other on the basis of the transferred treatment plans. Preferably, prior to carrying out any treatment or diagnosis, the user modifies at least one value or data in at least one of the transferred treatment plans, in particular with a setting device of the dental or dental-surgical treatment or diagnosis device described above. Creating multiple treatment plans for multiple treatments or diagnoses, and preferably transferring multiple treatment plans to a (single) treatment or diagnosis device in a single transfer operation, advantageously increases ease of use by eliminating the need for a user to create each treatment plan individually, in particular via the setting device of the dental or dental-surgical treatment or diagnosis device.

Preferably, the at least one data set is encrypted before web-based transfer via the Internet and a cloud computing network and decrypted after web-based transfer. The dental or dental-surgical treatment or diagnosis device and the cloud computing network each additionally have software for encryption and/or decryption for this purpose. This advantageously ensures the secure transfer of the at least one data set, in particular of the patient data contained therein.

A preferred (computer-implemented) method for creating a treatment plan for a dental-surgical implantation in which at least one data set is transferred between a dental-surgical treatment device and an external memory element located outside the dental-surgical treatment device in a web-based manner via the Internet and a cloud computing network comprising the external memory element, comprises the following steps: (A) providing a remote control human-machine interface that is or becomes communicatively connected to the cloud computing network; (B) accessing a web application stored in the memory element of the cloud computing network to create a treatment plan for a dental-surgical implantation using the remote control human-machine interface; (C) entry and/or selection and/or modification of at least one data set and/or parameter value for the dental-surgical implantation via the accessed web application and transfer or storage of this data set and/or parameter value into the treatment plan; and (D) web-based transfer of the treatment plan (comprising the at least one data set and/or parameter value) via the Internet from the cloud computing network to the dental-surgical treatment device, in particular to an (internal) memory element of the dental-surgical treatment device.

This advantageously makes it possible for the user to create a treatment plan for a dental-surgical implantation independently of time and place and without restriction to a specific remote control human-machine interface.

Preferably, the memory element of the cloud computing network stores an implant library, in particular an implant library described above. Preferably, method step (C) described above comprises the selection of an implant from the implant library via the web application and the remote control human-machine interface, in particular an implant to be implanted in the dental-surgical implantation. The selection of the implant is made, for example, by the implant designation and/or the tooth position (according to the tooth scheme) for which the implant is intended in the implant library. Particularly preferably, the selection of the implant determines at least one data set and/or treatment value assigned to the implant, for example a torque value with which the implant is to be set, a maximum torque value with which the implant may be set, and/or a transmission ratio of a gear of a dental contra-angle handpiece with which the implant is to be set, and enters or incorporates this (automatically) in the treatment plan. The provision of an implant library thus considerably simplifies the creation of a treatment plan.

Preferably, the memory element of the cloud computing network stores software or a database for patient or treatment documentation or for patient management, in particular with information about a patient as described above. Preferably, the method described above for creating a treatment plan for a dental-surgical implantation comprises the additional step of linking the treatment plan with information on the patient to be treated and/or information on an implant to be implanted, in particular from the aforementioned software or database, and/or storing the treatment plan and/or treatment data in the aforementioned software or database. The provision of a software package or a database for patient or treatment documentation or for patient management thus considerably simplifies the documentation of a dental-surgical treatment.

It is preferably further provided that the dental-surgical treatment device comprises a controller for controlling or regulating the dental-surgical treatment device and/or a dental-surgical instrument connectible to it. Preferably, the dental-surgical implantation and/or the instrument required for it, for example a dental-surgical contra-angle handpiece, is/are controlled by the controller on the basis of the treatment plan transferred via the Internet and web (and stored in the internal memory). This saves the user the tedious configuration of the required operating parameters on the dental-surgical treatment device via keys and similar operating elements.

Preferably, the method described above for preparing a treatment plan for a dental-surgical implantation comprises the preparation of a plurality of treatment plans, in particular for different patients, in accordance with steps (A)-(C), and the web-based transfer of this plurality of treatment plans in accordance with step (D) to one or more dental-surgical treatment devices, in particular to its/their (internal) memory element(s). Preferably, the plurality of treatment plans is sent to the dental-surgical treatment device as one data set or data package. This significantly simplifies the creation of treatment plans, as one user can create and transfer a plurality of treatment plans at once, for example for the entire coming day.

In another preferred (computer-implemented) method for the web-based transfer of at least one data set between a dental-surgical treatment device and an external memory element located outside the dental-surgical treatment device via the Internet and a cloud computing network comprising the external memory element, the at least one data set comprises measurement, operating, or treatment data required for a dental-surgical implantation, in particular control data or control values such as at least one torque or rotational speed value, wherein the at least one data set is sent from the cloud computing network, in particular from the external memory element, via the Internet to the dental-surgical treatment device. This advantageously makes it possible for the user to set implantation values independently of time and place and without restriction to one dental-surgical treatment device.

In a further preferred (computer-implemented) method for the web-based transfer of at least one data set between a dental-surgical treatment device and an external memory element located outside the dental-surgical treatment device via the Internet and a cloud computing network having the external memory element, the at least one data set comprises measurement, operating, or treatment data measured, detected, and/or generated during a dental-surgical implantation, wherein the at least one data set is sent from the dental-surgical treatment device through the Internet to the cloud computing network, in particular to the external memory element. This advantageously makes it possible for the user to retrieve the at least one data set independent of time and place and without restriction to a specific remote-control human-machine interface.

The measurement, operational, or treatment data of the present method generally comprise at least one of the data or values referred to above, preferably the technical data or values of a parameter and/or the non-technical data or values referred to. Particularly preferably, the measurement, operational, or treatment data comprise one or more torque values measured during implant placement, in particular by a sensor of the dental-surgical treatment device referred to above, or a torque curve generated from the individual measured torque values. Preferably, the measurement, operating, or treatment data comprise a time and/or date, in particular for proving when the dental-surgical implantation took place and/or when the measurement, operating, or treatment data were generated and/or sent.

In another preferred (computer-implemented) method for the web-based transfer of at least one data set between a dental or dental-surgical treatment device and an external memory element located outside the dental or dental-surgical treatment device by the Internet and a cloud computing network having the external memory element, the at least one data set comprises at least one measured value of the stability of a (dental) implant fixed in a bone, wherein the at least one data set is sent from the dental-surgical treatment device through the Internet to the cloud computing network, in particular the external memory element. This advantageously makes it possible for the user access the at least one measured value of the implant stability independent of time and place and without restriction to a specific remote-control human-machine interface.

Preferably, the at least one data set, in particular the data set having the measurement, operating, or treatment data or the measured value of the implant stability, comprises a value or an indication transferred to the dental or dental-surgical treatment device prior to the dental or dental-surgical treatment or diagnosis, for example implantation, in particular in a web-based manner via the Internet and the cloud computing network comprising the external memory element. For example, the data is for identifying the patient and was transferred to the dental surgical treatment device with a treatment plan prior to dental implantation. This advantageously makes it possible to precisely assign the at least one data set.

The method for the web-based transfer of the at least one data set preferably comprises the further step that the at least one data set, in particular the data set having the measurement, operating, or treatment data or the measured value of the implant stability, is temporarily stored in an internal memory element of the dental or dental-surgical treatment or diagnosis device and/or in a memory element of a transmitting and receiving device transmitting the measurement, operating, or treatment data in a web-based manner before the web-based transfer to the dental or dental-surgical treatment or diagnosis device. The transmitting and receiving device is implemented as a router or gateway, for example. The above-mentioned memory elements advantageously form a data buffer in order to prevent the loss of data in particular if, for example, the web-based data transfer to the cloud computing network is interrupted.

The method for web-based transfer of the at least one data set preferably comprises the further step that a remote-control human-machine interface communicatively connected to the cloud computing network is provided and that, in particular, the at least one data set, having been transferred from the dental or dental-surgical treatment or diagnosis device via the Internet to the cloud computing network, in particular the external memory element, is displayed and/or retrieved and/or processed by the remote control human-machine interface. The transferred data set can also be printed and/or forwarded to another electronic device. By storing the at least one data set in the cloud computing network, it is advantageously possible to access said data set independent of time and place and without being restricted to a particular remote human-machine interface.

Preferably, the memory element of the cloud computing network stores software or a database for patient or treatment documentation or for patient management, in particular having information about a patient as described above. Preferably, the method described above for the web-based transfer of at least one data set comprises the further step of linking the at least one transferred data set to information about the (treated) patient, in particular from said software or database, and/or storing the at least one transferred data set in the software or database for patient or treatment documentation or for patient management. The linking or storage preferably takes place automatically, in particular on the basis of patient identification data contained in the at least one web-based data set. The present method step thus considerably simplifies the documentation of a dental-surgical treatment.

The method for the web-based transfer of the at least one data set preferably comprises the further step that the data set, in particular the data set having the measurement, operating, or treatment data or the measured value of implant stability, is provided with a date and/or time indication (date or time stamp) prior to web-based transfer to the cloud computing network. Preferably, the transmitting and receiving device of the dental or dental-surgical treatment or diagnosis device is configured to add the date and/or time indication to the data set. Preferably, the transmitting and receiving device has its own electronic date and/or time measuring device (timer and/or controller) or is configured to access an online date and/or time source. The transmitting and receiving device is implemented as a router or gateway, for example. The addition of a date and/or time indication advantageously facilitates the temporal documentation of the treatment or diagnosis.

The addition of a date and/or time indication is particularly advantageous in the method wherein at least one data set contains at least one measurement of the stability of an implant fixed in a bone. Preferably, the method also comprises determining a plurality of measured values of implant stability at intervals, in particular intervals of a plurality of days, weeks, or months. Preferably, a date and/or time indication is added to each of said data sets having an additional measured stability values. Preferably, the data sets having the measured stability value and the date and/or time indication are stored in the external memory element of the cloud computing network. Preferably, these transferred data comprising the measured stability value and the date and/or time indication and information on the (treated) patient, in particular from the software or database for patient or treatment documentation or for patient management, are or get linked and/or stored in said software or database. Preferably, the cloud computing network has software for (automatically) presenting the data sets having the measured stability value and the respective (associated) date and/or time indication of a patient, in particular for jointly (graphically) presenting the data sets in a diagram, preferably as a diagram in which the measured stability values are presented in relation to the course of time (based on the respective date and/or time indications of the data sets). Preferably, said representation can be displayed and/or retrieved via the remote-control human-machine interface. This advantageously provides the user with an overview of the course of implant stability over time, in particular the course of healing of a recently set implant.

For the method indicated, the dental or dental-surgical treatment or diagnosis device preferably comprises a device for determining the stability of a set implant, in particular for determining the quality of healing of the implant or the connection of the implant to the surrounding bone substance. Such a device for determining implant stability is especially configured to cause the implant to vibrate in a contact-free or contacting manner, e.g., magnetically or by means of sound waves. The device is also configured to for receive and process a response signal from the implant, in particular an oscillation, on the basis of which a measured value of the stability of an implant fixed in a bone, for example, the oscillation frequency, can be determined.

According to another (computer-implemented) method for creating an implant passport or implant ID card (for a patient), data on an implant (implanted or to be implanted) is stored in the external memory element of the cloud computing network, in particular in software or a database of the external memory element for patient or treatment documentation or for patient management. The data on the implant comprise for example at least one of the following data: Information on the manufacturer of the implant, in particular name, address, contact details, website; a serial number of the implant; a name and/or type and/or model of the implant; an expiration date by which the implant must be implanted; instructions for the recipient or wearer of the implant; or similar information. The data on the implant are preferably recorded by means of an image recording device, in particular a camera, in particular from a data store, for example a barcode, on the packaging of the implant. Alternatively, the data on the implant can be read from an electronic data memory, for example an RFID tag, on the packaging of the implant using a reading device. Preferably, the data on an implant (implanted or to be implanted) is linked to one or more data about the patient, i.e., the recipient of the implant, whereby the data about the patient is particularly preferably retrieved from the software or a database of the external memory element for patient or treatment documentation or for patient management.

The data of the implant is further preferably displayed and/or retrieved via a remote-control human-machine interface communicatively connected to the cloud computing network. In particular, the remote-control human-machine interface is used to issue the command to print out the data on the implant, preferably with at least one additional item of information on the patient, and thus to issue the implant passport or implant identification card.

Preferably, the method for creating an implant passport or implant identity card can be combined or integrated with one of the above (computer-implemented) methods for web-based transfer of at least one data set between a dental or dental-surgical treatment device and an external memory element located outside the treatment device via the Internet and a cloud computing network having the external memory element, or is designed as part of such a method for web-based transfer of at least one data set.

A computer program product is also provided which comprises instructions that, when executed by a computer, cause the computer to perform a method referred to or described above. The computer program product contains in particular at least one machine-readable program carrier on which a computer program or software is stored in the form of electronically and/or optically readable commands or control signals for executing a method referred to or described above.

A computer-readable storage medium is also provided which comprises instructions that, when executed by a computer, cause the computer to perform a method referred to or described above.

A dental or dental-surgical treatment or diagnosis system comprises a dental or dental-surgical treatment or diagnosis device, a cloud computing network having an external memory element located outside the dental or dental-surgical treatment or diagnosis device, and a data processing device (having means) for performing any of the above-mentioned or described methods. The dental or dental-surgical treatment or diagnosis device in particular comprises at least one of the treatment or diagnosis devices referred to above. Preferably, the cloud computing network comprises at least a part of the data processing device. In particular, a microcontroller of the cloud computing network forms at least a part of the data processing device.

Another dental or dental-surgical treatment or diagnosis system comprises a dental or dental-surgical treatment or diagnosis device and a transmitting and receiving device for communicatively connecting to a remote human-machine interface, wherein the transmitting and receiving device is configured to provide a web-based connection via the Internet and a cloud computing network to the remote human-machine interface. The dental or dental-surgical treatment or diagnosis device in particular comprises at least one of the treatment or diagnosis devices referred to above.

The dental or dental-surgical treatment or diagnosis systems advantageously enable a user to access a data set stored in the cloud computing network, in particular in the external memory element thereof, independent of time and place and without being restricted to a specific remote control human-machine interface.

The dental or dental-surgical treatment or diagnosis systems preferably comprise a transmitting and receiving device, in particular a router or a gateway. Preferably, the transmitting and receiving device, in particular the gateway, is configured for communicating wirelessly with the dental or dental-surgical treatment or diagnosis device. Preferably, the transmitting and receiving device, in particular the gateway, is configured to communicate wirelessly with a local network, in particular a local network in a dental or dental surgery practice. Preferably, the transmitting and receiving device, in particular the gateway, is connected or can be connected by wire to the cloud computing network. This advantageously creates a variable system for transferring at least one data set between the dental or dental-surgical treatment or diagnosis device and the external memory element of the cloud computing network, by either wired connection or wireless connection through the local network connected to the Internet.

The transmitting and receiving device, in particular the gateway, is preferably configured to provide a data set (in particular having a value measuring the stability of an implant fixed in a bone) transmitted via the gateway with a date and/or time indication, as already described above.

The transmitting and receiving device is formed either as a separate element that is at least communicatively connected to the dental or dental-surgical treatment or diagnosis device, or as an element integrated into the treatment or diagnosis device.

Preferably, the dental or dental-surgical treatment or diagnosis device has software for (wirelessly) pairing with the transmitting and receiving device.

These and other embodiments will be described below with reference to the following drawing.

BRIEF DESCRIPTION OF THE DRAWING

FIG. 1 shows a dental or dental-surgical treatment or diagnosis system comprising web-based transfer of a data set.

DETAILED DESCRIPTION

The treatment or diagnosis system 1 comprises a dental or dental-surgical treatment or diagnosis device 2 and a transmitting and receiving device 3 for communicatively connecting to a remote-control human-machine interface 4. The transmitting and receiving device 3 is configured to provide a web-based connection from the dental or dental-surgical treatment or diagnosis device 2 via the Internet and a cloud computing network 5 to the remote control human-machine interface 4.

The dental or dental-surgical treatment or diagnosis device 2 is shown in FIG. 1 as a table-top dental-surgical device, in particular for carrying out dental-surgical interventions, preferably implantations. However, it is expressly noted that the dental or dental-surgical treatment or diagnosis device 2 may comprise a variety of other devices, such as a handpiece, a contra-angel handpiece, a device for determining the stability of a set implant, or a dental or dental-surgical treatment unit.

The dental or dental-surgical treatment or diagnosis device 2 comprises a display device 2A for displaying data, in particular comprising values, parameters, and/or data of the at least one data set transferred in a web-based manner. The dental or dental-surgical treatment or diagnosis device 2 comprises at least one control element 2B in order to be able to change values, parameters, and/or data, in particular of the at least one data record transferred in a web-based manner.

Through a web-based connection 6 between the cloud computing network 5 and the dental or dental-surgical treatment or diagnosis device 2, at least one data set having one or more values, parameters, or specifications is transferred. The transfer of at least one data set via the web-based connection 6 is in particular bidirectional, as symbolized by the two-sided arrow 6.

The cloud computing network 5 comprises at least one external memory element 5A in which the at least one data set can be stored. The cloud computing network 5 in particular comprises further hardware and/or software elements, for example a microcontroller and one or more software programs or web applications which in particular can be executed by the microcontroller. The web application can be called up and/or operated via the remote-control human-machine interface.

The remote-control human-machine interface may optionally comprise, for example, a mobile electronic device 4A, in particular a mobile telephone, or a stationary electronic device 4B, in particular a personal computer.

A web application stored in the cloud computing network 5, in particular in the external memory element 5A, is called up using the remote-control human-machine interface 4 in order to retrieve and/or display and/or process at least one data set stored in the external memory element 5A and/or to enter at least one data set and store said data set in the external memory 5A. The remote-control human-machine interface 4 comprises a web browser for accessing the web application.

The bidirectional communication link between the remote control human-machine interface 4 and the cloud computing network 5 is also web-based and labeled as reference 7.

The web-based communication connections 6 and 7 are wireless and/or wired.

Through the treatment or diagnosis system 1 it is possible to perform one or more of the methods described above for transferring at least one data set between a dental or dental-surgical treatment or diagnosis device 2 and an external memory element 5A located outside the dental or dental-surgical treatment or diagnosis device, which will not be described again in detail in order to avoid repetition.

The embodiment described and shown serves in particular for illustrating the invention. The features disclosed in the embodiment are therefore not limited to the present embodiment, but can rather be combined individually or together with one or more features of one or more other embodiments described.

What is claimed is:

1. A method of controlling a dental treatment device for implantation arranged in a medical treatment environment, the dental treatment device comprising a programmed control device controlling a motor of a treatment tool for use in setting an implant, and an internal memory storing one or more treatment plans for implantation of an implant to be implemented by the programmed control device, wherein the method comprises:
    providing an external memory element located in a hardware environment of a cloud computing network, wherein the hardware environment with the external memory element is physically separated from and external to the medical treatment environment, the external memory element storing software for planning a treatment with the dental treatment device for implantation;
    providing a remote-control human-machine interface communicatively connected to the external memory element located in the cloud computing network;
    utilizing the remote-control human-machine interface to access the software for planning a treatment and to enter and/or modify a treatment plan for implantation of an implant in the external memory element, wherein the treatment plan comprises at least one of the following data: a torque value, a torque limit value, a speed value, a speed limit value, a transmission ratio of a mechanical gear of the dental or dental-surgical treatment device, a volume flow of an operating or cooling medium;
    transferring the treatment plan for implantation of an implant from the external memory element to the internal memory of the dental treatment device for implantation, wherein the treatment plan for implantation of an implant via the Internet; and
    operating the dental treatment device for implantation by controlling the motor with at least one of the data of the treatment plan for implantation of the implant, wherein the data of the treatment plan comprises at least one of torque value, torque limit value, speed value, speed limit value, transmission ratio of a mechanical gear of the dental or dental-surgical treatment device, or volume flow of an operating or cooling medium.

2. The method of controlling according to claim 1, further comprising
    a bidirectional transfer of the treatment plan for implantation of an implant between the dental treatment device for implantation and the external memory element, such that the treatment plan for implantation of an implant is transferred back to the external memory element.

3. The method of controlling according to claim 1, wherein
    the treatment plan for implantation of an implant comprises information about an implant to be implanted.

4. The method of controlling according to claim 1, wherein
    a web application stored in the cloud computing network is called up through the remote control human-machine interface and the treatment plan for implantation of the implant in the external memory element is processed, entered, modified or stored by the web application.

5. The method of controlling according to claim 1, wherein
    the treatment plan for implantation of an implant is processed by a microcontroller of the cloud computing network.

6. The method of controlling according to claim 1, wherein
    the external memory element stores an implant library with data or values for a plurality of implants.

7. The method of controlling according to claim 1, wherein
    the treatment plan for implantation of an implant transferred via the Internet comprises operating data or at least one value of an operating parameter of the dental treatment device for implantation.

8. The method of controlling according to claim 1, wherein
    the external memory element stores patient data which get assigned to the treatment plan for implantation of an implant transferred via the Internet.

9. The method of controlling according to claim 1, wherein
    the dental treatment device for implantation comprises a setting device separate from the remote-control human-machine interface and separate from the external memory element, wherein the treatment plan for implantation of an implant is transferred by the Internet and is stored in the internal memory of the dental treatment device for implantation, and wherein at least one value or parameter of the treatment plan for implantation of an implant of the treatment plan for implantation of an implant stored in the memory is changed with the setting device.

10. The method of controlling according to claim 1, wherein
    the dental treatment device for implantation comprises the internal memory element for storing the treatment plan for implantation of an implant transferred via the Internet, wherein the internal memory element is further configured to buffer a data set to be transferred by the Internet from the internal memory element to the external memory element.

11. The method of controlling according to claim 1, wherein
the treatment plan for implantation of an implant is encrypted before transfer via the Internet and decrypted after the transfer by the internet.

12. A non-transitory computer program product or computer-readable storage medium comprising instructions which, when executed by a computer, cause the computer to execute the method according to claim 1.

13. A dental treatment system, comprising
a dental implantation device,
a cloud computing network having an external memory element located outside the dental treatment device for implantation, and
a device for data processing having means for executing the method according to claim 1.

14. The dental treatment system according to claim 13, further comprising
a remote control human-machine interface communicatively connected to the cloud computing network and configured to display and/or retrieve and/or process a treatment plan for implantation of an implant stored in the external memory element.

15. One or more non-transitory computer readable storage media storing instructions that, when executed by one or more processors, cause the one or more processors to perform a method for implementing a treatment plan for a dental-surgical implantation, the method comprising:
coupling a remote control human-machine interface to a cloud computing network;
receiving instructions via the remote control human-machine interface to access a web application stored in an external memory of the cloud computing network;
generating the treatment plan for the dental-surgical implantation with the web application based on input received from the remote control human-machine interface, wherein generating the treatment plan comprises setting at least one of the following values for the treatment plan for the dental-surgical implantation: torque value, torque limit value, speed value, speed limit value, transmission ratio of a mechanical gear of the dental treatment device, or volume flow of an operating or cooling medium;
implementing a web-based transfer of the treatment plan updated with at least one value for the dental-surgical implantation to a dental-surgical implantation device;
updating an internal memory of the dental-surgical implantation device with the treatment plan updated with the at least one value for the dental-surgical implantation; and
operating the dental-surgical implantation device to control a motor of the dental-surgical implantation device with at least one of the data of the treatment plan stored in the internal memory of the dental-surgical implantation device to set an implant: torque value, torque limit value, speed value, speed limit value, transmission ratio of a mechanical gear of the dental implantation device, volume flow of an operating or cooling medium.

16. The one or more computer readable media of claim 15, wherein the treatment plan for the dental-surgical implantation comprises at least one value or data from an implant library.

17. The one or more computer readable media of claim 15, wherein generating the treatment plan based on input received from the remote control human-machine interface comprises receiving an input designating an implant from an implant library stored in the cloud computing network.

18. The one or more computer readable media of claim 15, wherein after updating the internal memory of the dental-surgical implantation device, the at least one value for the dental-surgical implantation is modified with a setting device of the dental-surgical implantation device.

19. The one or more computer readable media of claim 15, wherein the at least one value for the dental-surgical implantation comprises at least one treatment value.

20. The one or more computer readable media of claim 15, wherein the at least one value for the dental-surgical implantation comprises at least one of a torque value at which a selected implant is to be set, a maximum torque value with which a selected implant can be set or a transmission ratio of a gear of a handpiece with which a selected implant can be set.

21. The one or more computer readable media of claim 15, further comprising linking the treatment plan for the dental-surgical implantation with patient information for a specific patient.

22. The method of controlling according to claim 6, wherein
an implant to be implanted with at least one treatment value assigned to the implant to be implanted is selected from the implant library via the remote control human-machine interface and entered into the treatment plan for implantation of an implant.

23. The method of controlling according to claim 1, wherein
at least one data set comprising at least one measured value of the stability of an implant fixed in a bone is sent from the dental treatment device for implantation through the Internet to the external memory element of the cloud computing network.

24. A method for implementing a treatment plan for a dental-surgical implantation comprising:
providing a dental treatment device arranged in a medical environment, the dental treatment device comprising a programmed control device controlling a motor of a treatment tool for use in setting an implant, and an internal memory storing one or more treatment plans for implantation of an implant to be implemented by the programmed control device;
providing an external memory element in a hardware environment of a cloud computing network comprising the external memory element, wherein the hardware environment with the external memory element is physically separated from and external to the medical treatment environment;
providing a remote control human-machine interface that is selectively communicatively connected to the cloud computing network, the remote control human-machine interface accessing a web application stored in the external memory element and creating a select treatment plan for a dental-surgical implantation comprising entry and/or selection and/or modification of at least one data set and/or parameter value for the dental-surgical implantation and transfer or storage of this data set and/or parameter value into the select treatment plan;
implementing a transfer of the select treatment plan comprising the at least one data set and/or parameter value via the Internet from the external memory element of the cloud computing network to the internal memory element of the dental treatment device; and operating the dental treatment device to control setting of an implant by controlling the motor with the at least one data set and/or parameter value of the select treatment plan stored in the internal memory of the dental treatment device, wherein the at least one data set and/or parameter value comprises at least one of torque value, torque limit value, speed value, speed limit value, transmission ratio of a mechanical gear of the dental treatment device, or volume flow of an operating or cooling medium.

25. A method for implementing a treatment plan according to claim 24, wherein the external memory element stores an implant library with data or values for a plurality of implants, wherein an implant to be implanted with at least one data set and/or treatment value assigned to the implant to be implanted is selected from the implant library via the web application and the remote control human-machine interface and entered into the treatment plan.

26. A method for implementing a treatment plan according to claim 24, wherein after operating the dental treatment device for implantation, operating data or at least one value of an operating parameter of the dental treatment device for implantation newly generated during operation of the dental treatment device are transferred in a web-based manner via the Internet and a cloud computing network to the external memory element.

* * * * *